US010849518B2

(12) United States Patent
Hartings et al.

(10) Patent No.: US 10,849,518 B2
(45) Date of Patent: Dec. 1, 2020

(54) NON-INVASIVE DETECTION OF SPREADING DEPOLARIZATION USING SCALP ELECTROENCEPHALOGRAPHY

(71) Applicant: University of Cincinnati, Cincinnati, OH (US)

(72) Inventors: Jed A. Hartings, Cincinnati, OH (US); J. Adam Wilson, Maineville, OH (US); Jason M. Hinzman, Taylor Mill, KY (US); Norberto Andaluz, Cincinnati, OH (US); Vincent DiNapoli, Cincinnati, OH (US); Sebastian Pollandt, Chicago, IL (US)

(73) Assignee: University of Cincinnati, Cincinnati, OH (US)

( * ) Notice: Subject to any disclaimer, the term of this patent is extended or adjusted under 35 U.S.C. 154(b) by 759 days.

(21) Appl. No.: 15/323,130

(22) PCT Filed: Jun. 30, 2015

(86) PCT No.: PCT/US2015/038430
§ 371 (c)(1),
(2) Date: Dec. 30, 2016

(87) PCT Pub. No.: WO2016/003966
PCT Pub. Date: Jan. 7, 2016

(65) Prior Publication Data
US 2017/0135594 A1    May 18, 2017

Related U.S. Application Data

(60) Provisional application No. 62/018,909, filed on Jun. 30, 2014, provisional application No. 62/035,756, filed on Aug. 11, 2014.

(51) Int. Cl.
*A61B 5/0476* (2006.01)
*A61B 5/04* (2006.01)
*A61B 5/00* (2006.01)

(52) U.S. Cl.
CPC ........ *A61B 5/04012* (2013.01); *A61B 5/0476* (2013.01); *A61B 5/4094* (2013.01)

(58) Field of Classification Search
CPC .. A61B 5/04012; A61B 5/0476; A61B 5/4094
See application file for complete search history.

(56) References Cited

U.S. PATENT DOCUMENTS

| 8,840,562 B2 * | 9/2014 | McKenna | ............ | A61B 5/6816 |
| | | | | 600/500 |
| 2010/0168532 A1 | 7/2010 | Waziri et al. | | |

(Continued)

OTHER PUBLICATIONS

Drenckhan, C. et al, Correlates of spreading depolarization in human scalp electroencephalography; Brain 135.3 (2012): 853-868; figures 1-3; pp. 853-865.

(Continued)

*Primary Examiner* — Puya Agahi
(74) *Attorney, Agent, or Firm* — Dinsmore & Shohl LLP (57) ABSTRACT

Non-invasive electroencephalogram (EEG)-based methods for detecting a spreading depolarization secondary to a brain injury in a patient who exhibits high-amplitude delta activity in at least one channel of a scalp EEG of an injured brain hemisphere of the patient include (a) recording a baseline scalp EEG pattern in the patient at a channel exhibiting high amplitude delta activity; (b) recording a continuous scalp EEG pattern in the patient across a time frame at the at least one channel; and (c) detecting a spreading depolarization during the time frame by observing at least one feature indicative of a spreading depolarization in the continuous scalp EEG recording pattern relative to the baseline scalp EEG pattern at the at least one channel. Scalp EEG record- (Continued)

ings are time-compressed prior to analysis. Methods of treating brain-injured patients and triaging brain-injured patients apply the non-invasive EEG methods.

14 Claims, 8 Drawing Sheets

(56) References Cited

U.S. PATENT DOCUMENTS

2012/0143020 A1   6/2012  Bordoley et al.
2014/0074060 A1*  3/2014  Imran .................. A61M 5/1723
                                                                     604/503
2014/0148657 A1*  5/2014  Hendler ............... A61B 5/0478
                                                                     600/301

OTHER PUBLICATIONS

Hartings, J.A. et al, Spreading Depolarizations and Late Secondary Insults after Traumatic Brain Injury; Journal of Neurotrauma, Nov. 2009; 26: 1857-1866; p. 1865.

Dohmen, C. et al, Spreading depolarizations occur in human ischemic stroke with high incidence; Annals of Neurology 63.6 (2008: 720-728, entire document.

Fabricius, M. et al, Cortical spreading depression and peri-infarct depolarization in acutely injured human cerebral cortex; Brain 129.3 (2006): 778-790.

* cited by examiner

NON-INVASIVE DETECTION OF SPREADING DEPOLARIZATION USING SCALP ELECTROENCEPHALOGRAPHY

PRIORITY CLAIM

The present application claims priority under 35 U.S.C. § 119(e) to U.S. Provisional Application Ser. No. 62/018,909 filed Jun. 30, 2014, and U.S. Provisional Application Ser. No. 62/035,756, filed Aug. 11, 2014, the entire disclosures of which are incorporated herein by this reference.

GOVERNMENT INTEREST

This invention was made with government support under W81XWH-08-2-0016 awarded by the U.S. Department of Defense. The government has certain rights in the invention.

TECHNICAL FIELD

This technology pertains generally to the field of medical diagnostics, triage and treatment, and in particular to non-invasive methods for detecting spreading depolarizations secondary to a primary lesion in a brain-injured patient using non-invasive scalp electroencephalography (EEG), triaging patients according to urgency indicated by characteristics of the detected spreading depolarizations, and initiating treatment to inhibit spreading depolarizations where detected.

BACKGROUND

Clinical treatment of stroke and traumatic brain injury (TBI) is limited by the lack of methods to monitor pathologic mechanisms of secondary injury, in particular in the time frame of emergence. Presently, intracranial pressure is the only cerebral variable that is continuously monitored in clinical practice, and mainly in patients with severe TBI. Several other monitoring modalities are available but are not widely used due to their invasive nature and uncertain clinical value. Nonetheless, advances in neuromonitoring are required to identify neuronal pathomechanisms that are active in individual patients who might benefit from neuroprotective therapies. In epilepsy and cardiology, for instance, continuous electrophysiologic monitoring allows diagnosis of disease subtype, pathologic localization, and evaluation of treatment effects.

In stroke, the concept of the ischemic penumbra was also developed on the basis of electrophysiologic monitoring. Soon after arterial occlusion, neurons in the core ischemic region undergo terminal depolarization, as marked by a steep elevation in extracellular [K+] and silencing of spontaneous cortical activity. In penumbral tissue surrounding the core, there is also electrical silencing and loss of function, but cellular membrane polarization is initially preserved. Through time, transient tissue depolarizations are periodically ignited at the rim of the ischemic core and spread throughout the penumbra. These spreading depolarizations eventually become prolonged and evolve to terminal depolarizations, recruiting the vulnerable penumbra into the ischemic core. Thus, electrophysiologic characterization of time-dependent lesion growth also yielded the concept of secondary injury and raised the possibility of neuroprotective interventions.

The phenomena of terminal and spreading depolarizations of cerebral cortex were discovered in the 1940's by A. P. P. Leão. When a strong stimulus was applied to rabbit cortex, he described a "spreading depression of activity in the cerebral cortex", indicating loss of function, accompanied by a negative shift of the direct-current (DC) potential, indicating mass tissue depolarization. Since 2002, these same electrophysiologic tools have been applied clinically to investigate spreading depolarizations in the pathophysiology of acute brain injury in humans. In patients requiring craniotomies, electrode strips are placed on the cortical surface for subsequent electrophysiologic monitoring during intensive care. As in animals, frequent spreading depolarizations are observed as propagating shifts of DC potential and spreading depression of spontaneous cortical activity. In patients with aneurysmal subarachnoid hemorrhage (SAH), clusters of repetitive spreading depolarizations are associated with delayed cerebral ischemia, characterized by new neurologic deficits and cortical infarcts. In TBI, the occurrence of spreading depolarizations is an independent predictor of poor clinical outcome.

Accumulating evidence suggests that monitoring of spreading depolarizations could have similar value in acute brain injury as electrophysiological tools have in epilepsy and cardiology, given that real-time diagnosis of mechanism becomes possible. The current gold-standard method for detecting spreading depolarizations in brain injury patients is with invasive intracranial EEG. Because the prospect of non-invasive monitoring is appealing, previous investigators attempted to identify indices on scalp EEG recordings corresponding to spreading depolarizations identified using more invasive techniques, but such attempts have thus far been unsuccessful, mostly due to the more subtle features and lack of requisite saliency in scalp EEG data. The present requirement for invasive procedures has limited the application of monitoring to a small minority of patients. Clearly, non-invasive and point-of-care methods for detecting and monitoring spreading depolarizations remain a need in the art.

SUMMARY

Accordingly, the present disclosure provides methods for non-invasively identifying/detecting spreading depolarizations in brain-injured patients using scalp electroencephalography (EEG), enabling routine monitoring on a scale that provides an earlier time frame for interventions to reduce secondary damage caused by spreading depolarizations a greater percentage of brain-injured patients.

One embodiment provides a non-invasive scalp electroencephalogram (EEG)-based method of detecting a spreading depolarization secondary to a brain injury in a patient exhibiting high-amplitude delta activity in at least one channel of a scalp EEG of an injured brain hemisphere of the patient. The method comprises: (a) recording a baseline scalp EEG pattern in the patient at the at least one channel; (b) recording a continuous scalp EEG pattern in the patient across a time frame at the at least one channel; and (c) detecting a spreading depolarization during the time frame by observing at least one feature indicative of a spreading depolarization in the continuous scalp recording pattern relative to the baseline pattern at the at least one channel. The features are salient and observable in a time-compressed recorded pattern and include depressions in the high-amplitude delta activity and shifts in direct-current potential at one or more channels, in isolated or continuous form.

According to another embodiment, methods for treating a brain injury patient by reducing extent of injury secondary to a primary lesion are provided. The methods comprise: (a) initiating a continuous scalp EEG recording of the patient; (b) identifying at least one EEG channel exhibiting high-amplitude delta activity and recording a baseline EEG pattern at the at least one channel; wherein the recordings are translated to a compressed time scale; (c) monitoring the continuous scalp EEG recording at the least one channel for presence of a feature indicative of a spreading depolarization, wherein the feature comprises at least one of (i) a depression in the high-amplitude delta activity in the EEG recording relative to the baseline recording pattern, and (ii) a shift in direct-current potential in the EEG recording relative to the baseline recording pattern; and (d) initiating therapy effective to decrease one or both of frequency and duration of the detected spreading depolarization. A therapy may be specifically directed to the primary brain insult/lesion, or may be a neuroprotective therapy directed to reducing an extent of secondary injury caused by spreading depolarization.

A further embodiment provides methods for triage of brain injury patients. The methods comprise: (a) generating a continuous scalp EEG recording pattern for each of the patients; (b) identifying patients exhibiting high-amplitude delta activity in at least one EEG channel of a recorded EEG pattern; (c) monitoring the EEG recording of the identified patients at the at least one channel across a time frame; and assigning a degree of urgency to a patient exhibiting one or more isolated or continuous features indicative of a spreading depolarization at the at least one channel, the features selected from an depression in the high-amplitude delta activity, and a shift in direct-current potential across a time frame.

These and other embodiments will be further elaborated and clarified by reference to the following Drawings and Detailed Description

BRIEF DESCRIPTION OF THE DRAWINGS

FIG. 1. Illustration of isolated, continuous, and intermediate depressions of EEG amplitude induced by spreading depolarizations. A) Eight hours of time-compressed recordings from patient no. 8 illustrate the three types of EEG depressions for spreading depolarizations labeled 1-7. Depressions are seen in raw traces C3-P3 and T7-P7, but not in other channels of the ipsilateral hemisphere or corresponding contralateral channels. Depolarizations #6 and #7 each produce unique, isolated depressions in EEG channels C3-P3 and T7-P7 followed by full amplitude recovery before the next depolarization. Depolarization #2 illustrates a continuous-type depression since the EEG depression initiated by depolarization #1 is continued when the second occurs 29 min later. Depolarizations #4 and #5 illustrate intermediate cases in which EEG amplitude recovery from prior depolarizations is only partial and a relative depression is maintained. Power integrals for channels C3-P3 and T7-P7 are shown illustrating the depression periods and spreading nature (arrows) of depolarizations #6 and #7. Amplitude fluctuations are also visualized in the compressed spectral array, a quantitative technique commonly used in continuous EEG. B) Representative traces from time points marked with red dotted lines in A, shown on an expanded time scale (10 s each). Notably, the two EEG channels in which depressions are observed have high baseline amplitudes with prominent polymorphic delta activity. In the depressed state, these waves are suppressed such that amplitudes are similar to other EEG channels. C) Pie chart shows the relative proportion of all 455 ECoG-identified spreading depolarizations with EEG manifestations characterized as the three types illustrated in A.

FIG. 2. Illustrates that slow potential changes accompany amplitude depressions as EEG signatures of spreading depolarizations. From the start of EEG in patient no. 15, 42 spreading depolarizations were identified in ECoG recurring at intervals of 34 min (median; IQR 29-38) over a period of 27 h beginning 3.6 days post-trauma. During this time, clear EEG amplitude depressions could not be identified, although EEG amplitudes in Fp2-F4 and F4-C4 increased after depolarizations ceased. A) a panel showing a 7.5 h spanning a transition period. Top: ECoG traces show recurring spreading depolarizations evidenced by spreading shifts of the DC potential and depressions of high-frequency (HF, 0.5-50 Hz) activity. Bottom: Traces of high-pass filtered (0.5 Hz) EEG activity show increased amplitude (Fp2-F4 and F4-C4) and no change (C4-P4, Fp2-F8) after depolarizations end. Full-band (DC) referential recordings from EEG electrodes Fp2 and F4 show an unstable baseline with negative shifts time-locked to DC shifts of spreading depolarizations recorded by ECoG (arrows and dashed lines). Thus, individual spreading depolarizations are observed in EEG even when amplitude depression of 0.5-50 Hz activity does not cycle with each event, but rather is continuous. The asterick (*) denotes the marked state transition as depolarizations end: the slow potential stabilizes and the amplitude of 0.5-50 Hz activity increases. B) a panel showing a 3.3 h time frame from the same patient 4.6 days later. Channels and conventions are the same as in A. Here, DC shifts are observed at EEG electrode F4 in connection with two spreading depolarizations that produce isolated amplitude depressions in F4-C4 and Fp2-F4. The epileptologist report on continuous EEG findings states that "1-4 Hz frequency delta background is seen. At times, it appears to be relatively suppressed." These suppressions are clearly the depressions induced by spreading depolarizations. Scale bars apply to all traces of the same type.

FIG. 3. Illustration of the effect of recording derivation and frequency bands on EEG depressions. A) Maximal depression of total EEG power in bipolar recording channels compared to referential (monopolar) recordings from the electrode of the bipolar pair with greatest amplitude depression. Twenty-one comparisons are shown. B) Proportions of total power of baseline activity contributed by activity in the four frequency bands. Assessments were made prior to depolarization-induced EEG depression for three events in each of seven patients. Error bars show standard deviations. C) Degrees of depression as percentages of baseline power for each frequency band.

FIG. 4. Illustration of widespread propagation of spreading depolarization evidenced by spreading depression of continuous EEG. A) Schematic diagram and scout CT show positions of cortical electrode strip and scalp electrodes in patient no. 6 following partial resection of the right temporal lobe and evacuation of the right subdural hematoma. CT image shows diffuse subarachnoid hemorrhage and intraparenchymal hemorrhage in right frontal and temporal lobes. ECoG (black upper traces): In this 8.5 h recording segment, six spreading depolarizations are observed as evidenced by slow potential changes (dashed circles) in the near-DC ECoG recording that propagate from channel 2-3 to channel 4-5 and are accompanied by depression of 0.5-50 Hz activity. EEG: Five bipolar EEG channels from the same hemisphere are shown. Colored traces correspond to the power-integral calculations shown below and to the colored electrode positions in the head schematic diagram. Arrows indicate the clear amplitude depressions in channels Fp2-F4 and C4-P4 that occur in time-locked, one-to-one correspondence with the ECoG-identified spreading depolarizations.

Note, however, that depressions occur first in C4-P4 and other posterior channels and are followed, after a substantial time lag of 30-40 min, by frontal Fp2-F4, indicating spreading depressions of EEG activity induced by spreading depolarization. Note also that the 2nd and 3rd depolarizations occurring in rapid succession are manifested as unique depression periods in Fp2-F4 but as a single continuous depression in C4-P4. Scale bars apply to all traces of the same type. B) A 7.3-h recording from patient no. 17 is shown following the same conventions as in panel A. Electrode 1 (arrow) is seen in the CT scan following evacuation of a large right frontal intracerebral hematoma. Three spreading depolarizations are seen in ECoG recordings and each is accompanied by unique, isolated depressions in EEG channels throughout the hemisphere. Depressions begin in F4-C4 (blue), in near-synchrony with the electrode strip, and propagate posteriorly to P4-O2 (green) after delays of 57, 11, and 26 min. The changing delays suggest different origins for each depolarization wave.

FIG. 5. Sets forth spreading depolarizations identified by continuous EEG alone. A) 5.25 hour time frame from patients nos. 17 and 16 during which no ECoG recordings were obtained. Five recurring amplitude depressions are observed in channels Fp2-F4, F4-C4, C4-P4, and P4-O2. Depressions recur more frequently at 53-75 min intervals and do not spread as far posteriorly when compared to the example illustrated by FIG. 4B. Spread is clearly observed as a march in depression from frontal to central to parietal locations. B) 3.5 hour time frame from patients nos. 17 and 18 during which no EcoG recordings were obtained, eight cycling amplitude depressions occur at 25-30 min intervals in C3-P3 and, to a lesser extent, P3-O1. This illustrates a case in which depolarizations recurring at short intervals each produced an isolated-type depression instead of a single continuous, prolonged depression. No spread is evident in this case.

DETAILED DESCRIPTION

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not necessarily limited to these preferred aspects.

Unless defined otherwise, all technical and scientific terms used herein have the same meaning as commonly understood by one of ordinary skill in the art to which the presently-disclosed subject matter belongs.

Spreading depolarizations are pathophysiologic waves that occur spontaneously in the brain following neurologic insults such as brain trauma or stroke. They are believed to cause further brain damage secondary to the primary insult. Detecting spreading depolarizations in patients may be useful for assessing causes of neurologic symptoms, to guide treatments, and to improve brain injury patient outcomes.

The current gold-standard method for detecting spreading depolarizations in brain injured patients is with invasive intracranial EEG. The present disclosure provides methods for detecting spreading depolarizations using non-invasive scalp EEG monitoring/recording of the patient based on three complementary assessments of the scalp EEG recording. Surprisingly, features indicative of spreading depolarization became detectable in recorded EEG waveform patterns translated into compressed time frame recordings.

It was discovered that spreading depolarizations are manifested as depressions in pathologic high-amplitude delta activity recorded in the scalp EEG. Delta activity generally consists of oscillating electrical activity in the 0.1-4.0 Hz frequency band. Depression is assessed relative to baseline delta activity at a channel. Observed depression of delta activity reflecting spreading depolarizations may be transient (minutes) and temporally isolated in the case of "isolated" depolarizations characterized by a return to baseline prior to another depression. Depression may be "continuous" in the case of ongoing depolarization activity, characterized as two or more depressions before return of activity to baseline or establishment of a new baseline (FIGS. 1-5; Table 2). While it is known that spreading depolarizations can induce depressions in the amplitude of brain activity, the present investigators are the first to successfully identify spreading depolarizations in scalp EEG by a characteristic waxing and waning of pathologic high-amplitude delta activity, also known as polymorphic delta activity.

Spreading depolarizations are also associated with and may be identified in scalp EEG by shifts in direct-current (DC) potential. These shifts occur at arbitrarily low frequencies, from 0.0 to 0.05 Hz, below the recording bandwidth of conventional EEG amplifiers (>0.1 Hz). Shifts may also be isolated or continuous and in some cases overlapping in the case of ongoing repetitive depolarization activity. In the latter case, spreading depolarizations are identified by a continuously unstable, shifting DC baseline (FIG. 2).

Embodiments of a non-invasive electroencephalogram (EEG)-based method of detecting a spreading depolarization secondary to a brain injury in a patient exhibiting high-amplitude delta activity in at least one channel of a scalp EEG of an injured brain hemisphere of the patient are provided The methods comprise (a) recording a baseline scalp EEG pattern in the patient at the at least one channel; (b) recording a continuous scalp EEG pattern in the patient across a time frame at the at least one channel; and (c) detecting a spreading depolarization during the time frame by observing at least one feature indicative of a spreading depolarization in the continuous scalp recording pattern relative to the baseline pattern at the at least one channel. According to specific embodiments, the recordings from (a) and (b) are translated to compressed time scale recordings prior to step (c). In other specific embodiments, the channel is a bipolar channel. Features of waveform patterns of a recorded scalp EEG that have a high probability of indicating presence of a spreading depolarization include depressions in the high-amplitude delta activity across a depression period relative to the baseline pattern at the at least one channel, and shifts in direct-current potential at one or more channels. A depression period is defined as the period from the onset of a depression until recovery to a steady-state amplitude. The steady state amplitude includes restoration to baseline or recovery to a new baseline amplitude. wherein a depression period is defined from onset of a depression until recovery to a steady-state amplitude.

A third complementary feature that may be observed verifies the spreading character of a spreading depolarization and provides an assessment of scope and/or severity by observing spread of the changes described in (1) and (2) above from one channel location to another. Spread is indicated by a delay in the time of occurrence of changes in recordings obtained from different channel locations (FIG.

Figure 1A:
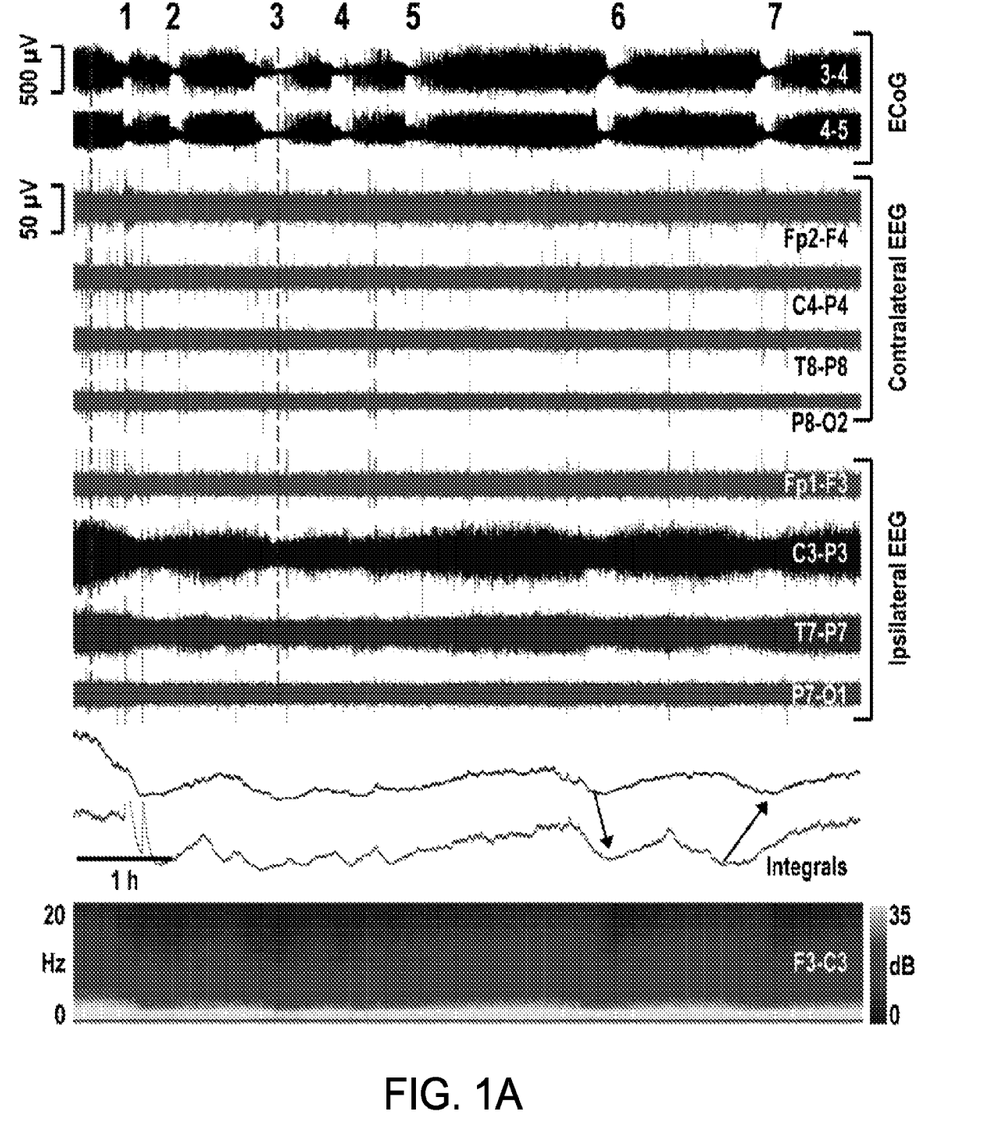
Figure 4A:
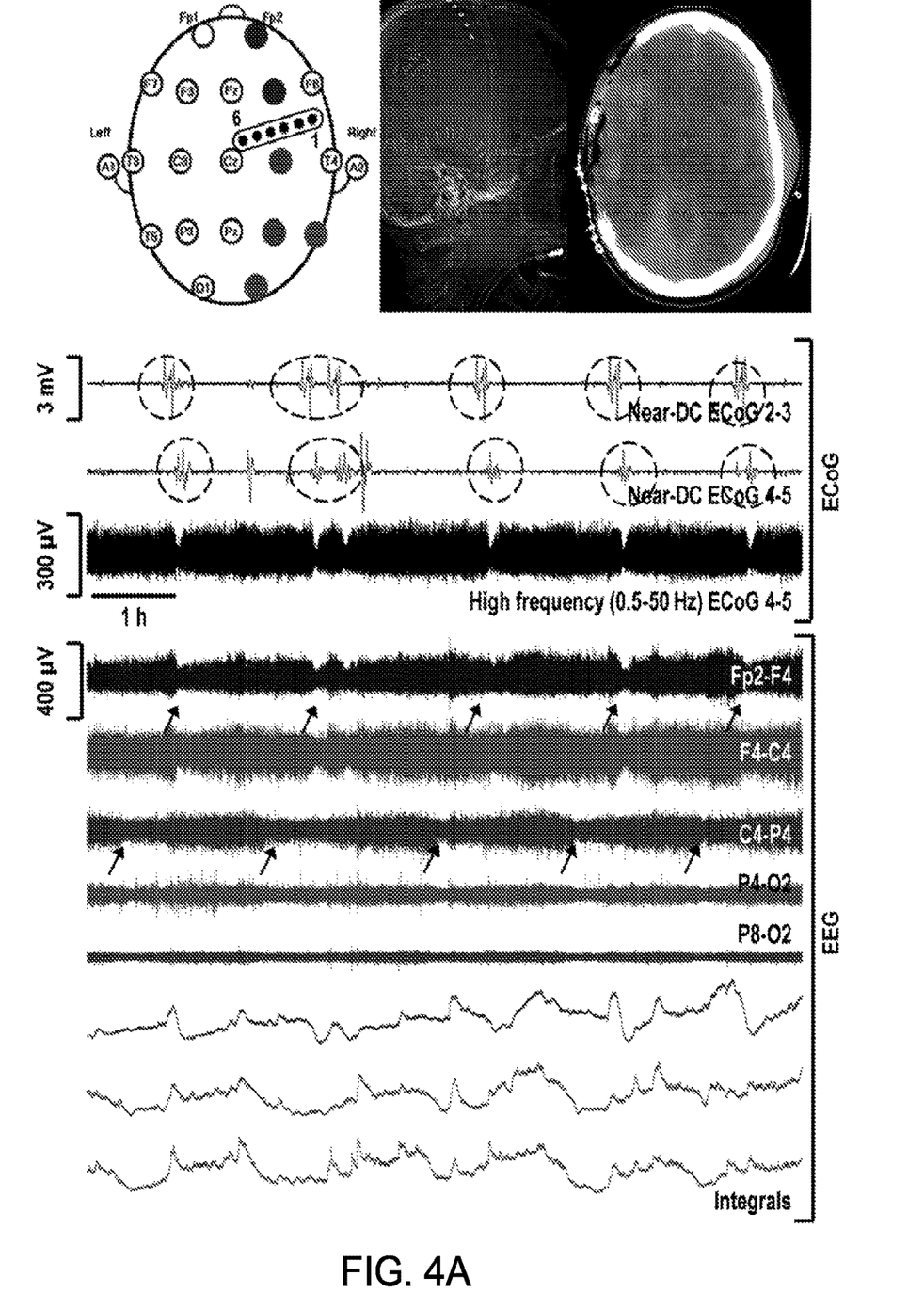
Figure 4B:
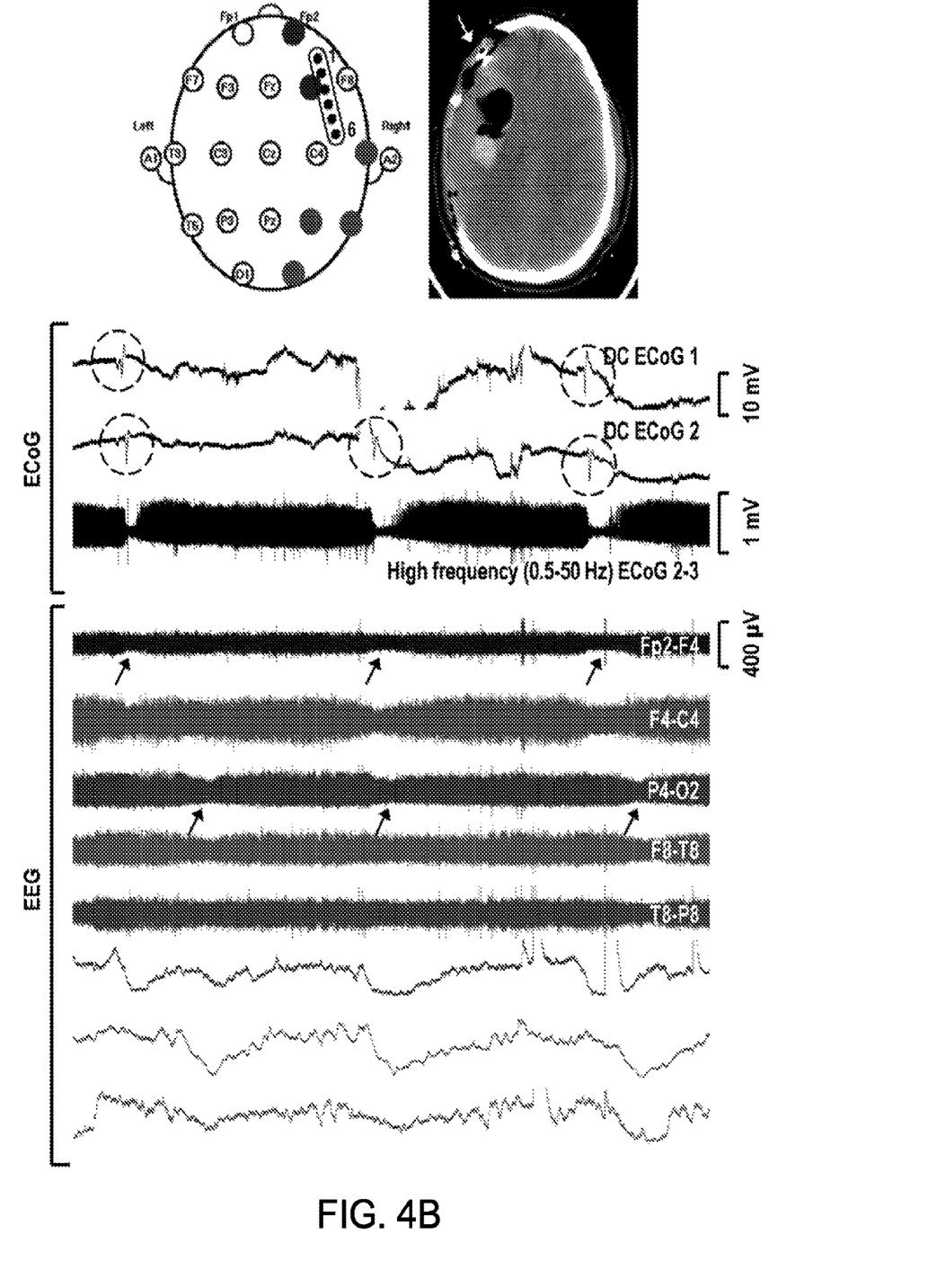
Figure 5A:
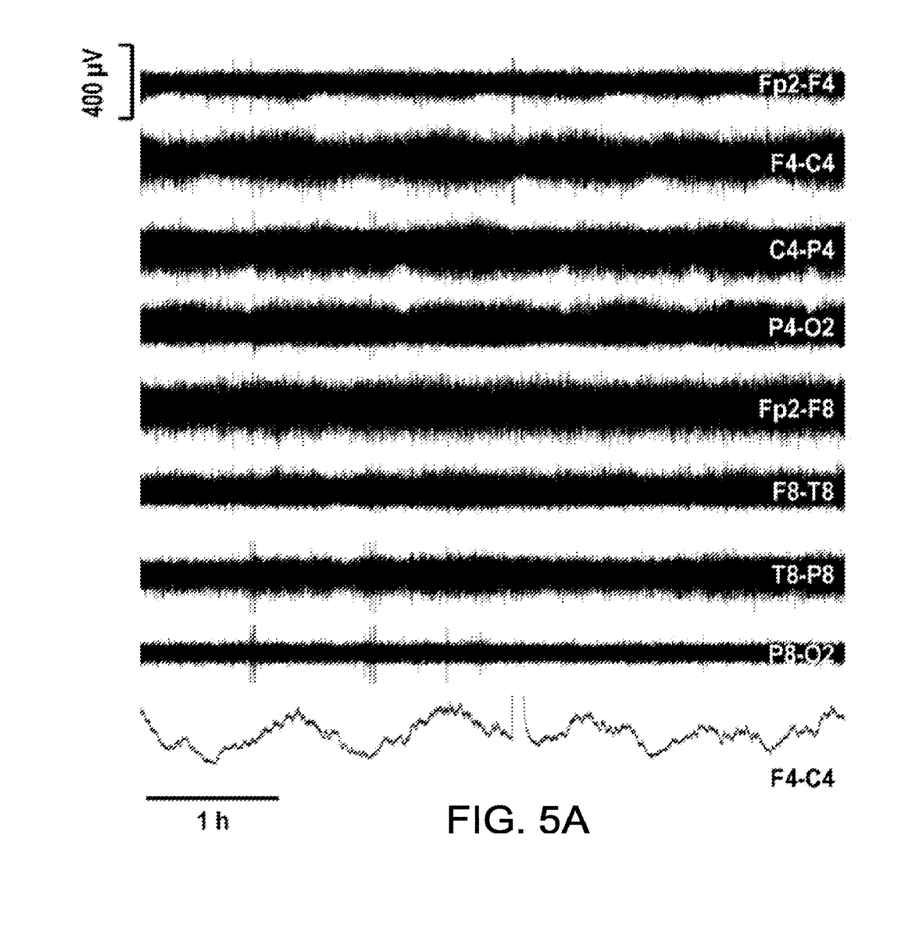

1A, FIG. 4, and FIG. 5A). In certain embodiments, a feature may be verified as spreading observing the feature in two or more channels with a time delay between onset of the feature in different channels. A spreading depolarization is more likely to cause secondary brain injury if it is verified as spreading between channels. In most cases, the relevant channels are intra-hemispheric, but it is contemplated that in very specific cases a spreading depolarization may cross from an injured hemisphere to a non-injured hemisphere.

By generating clinically standard non-invasive scalp EEG recordings over an extended time frame and translating the recording to a time-compressed recording, the vast majority of spreading depolarizations (>80%) recorded from the surface of cerebral cortex with the gold-standard ECoG technique were observed to manifest as depressions of high-amplitude delta activity in the EEG recordings. When intervals between depolarizations are long enough, they induce unique suppressions of this high-amplitude baseline such that amplitudes are normalized to levels in other channel regions. These depressions, attributable to individual depolarization waves, develop slowly and may persist up to an hour before the baseline EEG amplitude is fully restored. When depolarizations occur repetitively at short intervals, on the other hand, the depression of high-amplitude delta activity is maintained for longer periods, for example from hours to more than a day. It was further observed that Leão's "spreading depression of activity" can be observed in scalp EEG, since roughly one-third of spreading depolarizations produced depressions that spread with a temporal delay between EEG channels.

From the time of Leão's discovery in 1944, there was no evidence that spreading depolarizations could be observed non-invasively from scalp EEG until the recent report of Drenckhahn et al. [ ] In part, this was due to the belief that the spatial wavelength of spreading depression across the cortex was too short to influence EEG signals recorded from a much larger volume of tissue. However, it is estimated that scalp potentials reflect the synchronous activity of at least 6-10 $cm^2$ across brain's surface, which may include twice that area of cerebral cortex. Since spreading depolarization travels at 1-8 mm/min and depresses cortical activity for an average duration of 8 min, the typical spatial wavelength of depression is estimated at 0.8-6.4 cm. Assuming a wavefront width of >1 cm, and given that depressions can be arbitrarily long (hours), it was discovered that depolarizations can simultaneously depress the requisite volume of cortex to be observed in EEG.

Compared to intracranial electrodes, the larger recording area of scalp electrodes further explains the lesser degree of maximal EEG depression, the slower onset and recovery of depressions, and the longer total duration; only a subset of the total recording area is depressed at a given instant and more time is required for the wave to invade maximally and traverse the larger area. Similarly, continuous depression periods are explained by the fact that multiple depolarizations, when recurring at short intervals, may occur simultaneously in the same recording area and thus maintain a continuous cycle of partial depression. It is therefore likely that the failure to detect Leão's spreading depression through decades of EEG research in acute brain injury is attributable to the long durations of development, persistence, and spread. Recognition required viewing of long recording time frames on highly compressed time scales (40-90 mm/hr) that historically have not been used in clinical neurophysiology. Routine 30-min EEG exams reviewed at 10-30 mm/s preclude observation of events on this temporal scale.

As a measure of the brain's essential electrophysiologic function, EEG has long offered unrealized promise as a tool for monitoring the progression of intracranial pathology. The advantages of EEG over other neuromonitoring techniques include that it is non-invasive and continuous and assesses both regional and global cerebral status. Furthermore, quantitative analysis can facilitate interpretation of the large volumes of data generated. Long-term trending of alpha variability and other metrics, for instance, have been investigated as predictors of delayed cerebral ischemia in SAH patients.

Spreading depolarizations have now emerged as a new mechanism of delayed clinical deterioration in patients and as a target for EEG monitoring. In focal ischemia in the rat, a delayed phase of repetitive depolarization activity begins 6-10 h after stroke onset and coincides with the period of delayed infarct maturation. Importantly, these depolarizations recurring at short intervals did not produce unique depressions of spontaneous EEG activity, but rather were manifested as a continuous suppression of high-amplitude polymorphic delta activity. The occurrence of continuous depression periods in EEG recordings during temporal clusters of spreading depolarizations was since confirmed in SAH patients. As in animals, such clusters have a delayed onset and high positive and negative predictive value for delayed cerebral ischemia. It is now demonstrated that both isolated and continuous depressions of EEG amplitude induced by spreading depolarizations represent suppressions of pathologic high-amplitude delta activity, a common feature of all types of acute brain injury.

In recent years, continuous EEG has gained traction and is performed as standard-of-care at an increasing number of hospitals. The rationale for continuous, multi-day monitoring is primarily for the evaluation of subclinical seizures as a possible etiology for altered mental status or coma, taken with a belief that suppression of all early seizures, whether convulsive or non-convulsive, may improve outcomes. Compared to seizures, however, spreading depolarizations have a 3-7 fold higher incidence in patients. Furthermore, seizures and spreading depolarizations often occur with interacting patterns in the same tissue, and depolarizations may enhance epileptic activity by suppression of inhibitory neurotransmission. The present findings thus provide a new and complementary application for continuous EEG in acute brain injury.

In several respects, the instant results are similar to those reported by Drenckhahn in SAH patients. In that study, 47% of ECoG-identified spreading depolarizations induced isolated depressions in the scalp EEG, compared to 39% found here, and depressions reached 53% of baseline amplitude compared to 57% in the present study. In both studies, the remainder of depolarizations occurred at short intervals and did not induce unique depressions but rather maintained continuous depressions throughout temporal clusters of events, as noted above. Thus, the instantly disclosed results are reproducible across different centers and diseases and represent general features of acute brain injury.

However, the instant results differ in important respects. First, DC shifts were observed in scalp EEG for a majority (70%) of spreading depolarizations recorded by Drenckhahn, in contrast to only 15% in the four patients with DC-coupled EEG in the present study. Second, it was found that both EEG depressions and DC shifts spread between scalp electrodes with a temporal delay, while all changes occurred synchronously in Drenckhahn's SAH patients. The wide spatial extent of spreading depression presently observed was surprising, and further contrasts with a limited extent (<4.8 cm2) of depolarization propagation in border zones of malignant ischemic stroke. In specific embodiments, scalp EEG recordings utilize DC-coupled EEG amplifiers which, while not typically used in intensive care units, are presently under development for clinical application (Moberg Research, Inc.).

Validated scalp EEG methods for detection of spreading depolarizations provides the first non-invasive method for routine bedside monitoring of a neuronal pathomechanism and marker of lesion development with broad application to TBI and hemorrhagic and ischemic stroke.

EXAMPLE

Eighteen patients with acute TBI were enrolled from February 2009 to March 2013. Demographics and details of clinical course are given in Table 1. Lesions consisted mostly of contusions and subdural hematomas and all patients required neurologic surgery, despite a range of initial injury severities as indicated by Glasgow Coma Scale scores at hospital admission. In 17 of 18 cases, patients underwent large decompressive craniectomies. After surgery, ECoG recordings were made for 5.7 days (IQR 3.8-6.5) and the duration of simultaneous EEG and ECoG acquisition was 3.6 days (IQR 2.5-4.9). A total of 671 spreading depolarizations were observed in 15 of 18 patients during ECoG monitoring. Of these, 455 occurred during simultaneous EEG monitoring in 12 patients (Table 2) and were analyzed for EEG manifestations of spreading depolarizations.

Spreading depolarizations were identified in ECoG recordings according to methods previously described. Briefly, the signature of spreading depolarization is a negative shift of the DC potential, approximately 5-15 mV in amplitude in recordings with platinum electrodes and DC amplifiers. With AC amplifiers using 0.01 Hz high-pass cutoff, the DC shift appears as a slow-potential change of 1-5 mV peak-to-peak amplitude in the near-DC (<0.1 Hz) frequency band. These DC shifts or slow potentials propagate at 1-8 mm/min between electrodes and reflect in part the intracellular flux of cations during mass tissue depolarization. When spontaneous cortical activity is present (0.5-100 Hz band), the depolarization also causes amplitude depression in this higher frequency band and the depression spreads with the slow-potential. Thus, depolarizations were identified by spreading slow-potential changes in at least two electrodes with accompanying depression of spontaneous activity.

After first identifying depolarizations in ECoG recordings, EEG correlates were examined by review of time-aligned data. When ECoG and EEG were acquired in different systems (13 patients), recordings were temporally aligned by first importing each data set to MATLAB (The MathWorks, Inc., Natick, Mass.), and then exporting a combined file for analysis in LabChart (ADInstruments). For analysis of EEG, signals were examined on a highly compressed time scale of 40 to 90 mm per hour. Expanded, conventional time scales were also used to inspect signal quality and characterize baseline patterns. On compressed time scales, signals were visually inspected for amplitude depressions that occurred in association with depolarizations scored in ECoG channels and were not related to generalized amplitude shifts occurring throughout the relevant hemisphere. For each patient, characteristics of EEG depressions were quantified in a single channel chosen as the one exhibiting the greatest degree of amplitude modulation in connection with depolarizations. The power integral was calculated by squaring the signal and performing a leaky integration with a 120 s decay time constant. Maximum depression was measured as the percentage of the power integral at the trough of the depression period relative to the steady-state value before depression onset. The time to the trough of the power integral was also measured from the time of depression onset. Finally, the total depression time envelope, from beginning of depression to recovery to a steady-state amplitude, was measured based on both raw traces and power integrals. Data are reported as medians and interquartile ranges (IQR) and $p<0.05$ was considered statistically significant.

TABLE 1

Demographics and clinical characteristics

| No. | Age | Sex | Cause of TBI | GCS | Pupil React. | Lesions | Cran. Loc. | Flap Repl. | EEG/ECoG Start (d) | EEG/ECoG Dur. (d) | Analg./Sed. | Anti-Epileptic | SD in ECoG | 6-mo. GOS |
|---|---|---|---|---|---|---|---|---|---|---|---|---|---|---|
| 1 | 23 | F | MVA-P | 8 | 2 | L FT Cont, SDH | L | N | 0.6 | 3.7 | P, M, F | Ph, Lev | 19 | Good |
| 2 | 43 | M | Assault | 10 | 2 | Bilat F Cont (R > L) | R | N | 0.6 | 1.9 | M, F | Ph, Lev | 1 | Mod |
| 3 | 21 | M | MVA | 3 | 2 | Bilat F Cont | L, R | N | 3.3 | 2.8 | P, M, F, Lor | Ph, Lev | 34 | Veg |
| 4 | 23 | F | MVA | 3 | 0 | EDH, SAH | R | N | 0.6 | 5.3 | P, M, Lor | Ph, Lev | 4 | Severe |
| 5 | 74 | F | Fall | N/A | 0 | R F Cont, SDH | R | N | 0.9 | 2.2 | F | Lev | 12 | Dead |
| 6 | 44 | F | Fall | 7 | 2 | Bilat SDH (R > L) | R | N | 0.3 | 2.4 | P, M, F | Lev | 54 | Severe |
| 7 | 36 | F | MVA | 3 | 0 | R SDH | R | N | 0.8 | 4.9 | P, M, F | Lev | 1 | Severe |
| 8 | 38 | M | GSW | 15 | 1 | L MCA/ACA infarct | L | N | 2.8 | 3.0 | P, M, F | | 26 | Dead |
| 9 | 57 | M | Fall | 7 | 2 | R F Cont, ICH | R | N | 1.1 | 3.9 | P, M, F | Lev, Lor | 134 | Severe |
| 10 | 62 | M | Unk | 6 | 0 | R SDH | R | N | 1.0 | 2.8 | M, F | Lev | 0 | Veg |
| 11 | 46 | M | MC | 6 | 2 | R F Cont, SDH | R | Y | 1.0 | 4.4 | P, F | Lev | 71 | Severe |
| 12 | 65 | F | Fall | 6 | 2 | L SDH, Cont | L | N | 0.9 | 3.4 | M, F | Lev | 1 | Severe |
| 13 | 37 | F | Fall | 10 | 2 | L F Cont, SDH | L | N | 2.4 | 2.0 | F | Ph, Lev, Lor | 0 | Severe |
| 14 | 29 | M | Fall | 13 | 2 | Bilat Cont | Bif. | N | 0.8 | 0.9 | P, M, F | Lev | 0 | Mod |
| 15 | 27 | M | MVA-P | 8 | 2 | Bilat F Cont (L > R) | Bif. | N | 1.7 | 6.5 | F, Lor | Lev | 59 | Veg |
| 16 | 29 | M | Assault | 3 | 1 | L SDH | L | N | 1.4 | 4.9 | P, F, Lor | | 126 | Good |

TABLE 1-continued

Demographics and clinical characteristics

| No. | Age | Sex | Cause of TBI | GCS | Pupil React. | Lesions | Cran. Loc. | Flap Repl. | EEG/ ECoG Start (d) | EEG/ ECoG Dur. (d) | Analg./ Sed. | Anti-Epileptic | SD in ECoG | 6-mo. GOS |
|---|---|---|---|---|---|---|---|---|---|---|---|---|---|---|
| 17 | 30 | F | MVA | 9 | 2 | R F ICH | R | N | 0.5 | 6.2 | P, M, F | Ph, Lev, Lor | 122 | Severe |
| 18 | 74 | F | Fall | 15 | 2 | L T Cont, SDH | L | N | 1.3 | 4.9 | P, F | Lev | 7 | Severe |

Table 1: Causes of TBI include motor vehicle accident (MVA), pedestrian involved in motor vehicle accident (MVA-P), gunshot wound (GSW), and unknown (Unk). Glasgow Coma Scale (GCS) and pupillary reactivity were assessed at admission to the study hospital following resuscitation. For pupils, 2 = both reactive, 1 = one reactive, 0 = neither. Lesions include subdural hematoma (SDH), contusion (Cont), epidural hematoma (EDH), subarachnoid hemorrhage (SAH), and intracerebral hematoma (ICH) in frontal (F), temporal (T), or parietal (P) lobes of the left (L), right (R), or bilateral (Bilat) hemispheres. MCA = middle cerebral artery; ACA = anterior cerebral artery. Crantiotomy location (Cran. Loc.) is left (L), right (R), or Bifrontal (Bif.) and replacement of bone flap is indicated as yes (Y) or no (N). Start times and total durations of simultaneous EEG/ECoG recordings are given in days. Medications for analgesia and sedation were: P = propofol, M = midazolam, F = fentanyl and its analogues, Lor = lorazepam. Medications for seizure control or prophylaxis were: Ph = phenytoin or fosphenytoin, Lev = levetiracetam, Lor = lorezepam. The number of spreading depolarizations observed through whole duration of ECoG recordings is given. Outcomes at 6 months were assessed by the Glasgow Outcome Score (GOS) as good, moderate (mod) or severe disability, vegetative state (veg), or dead.

Figure 1B:
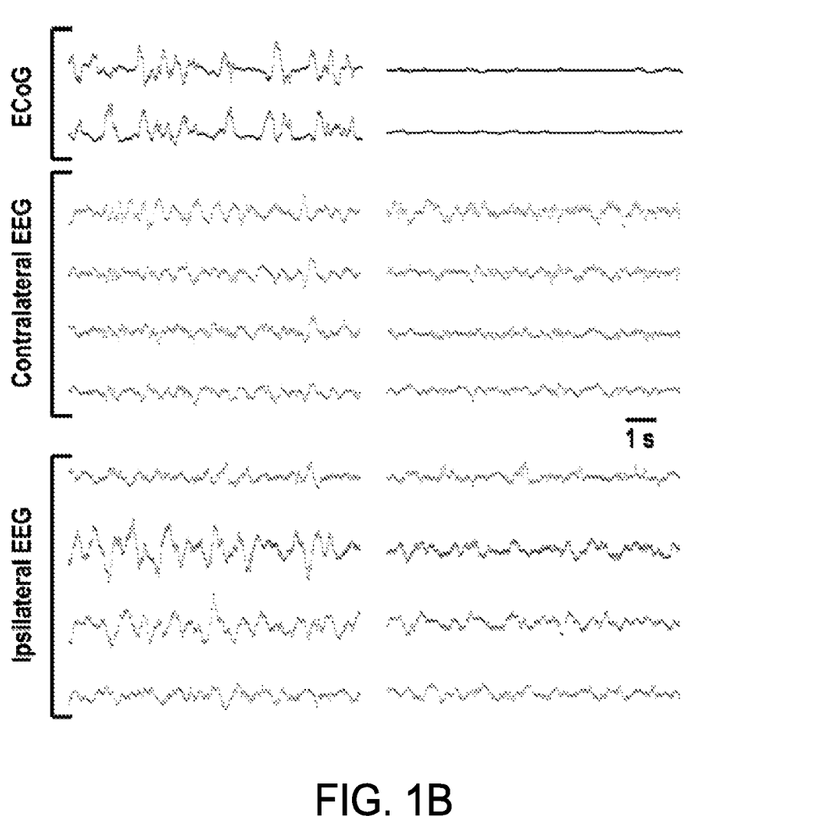
Figure 1C:
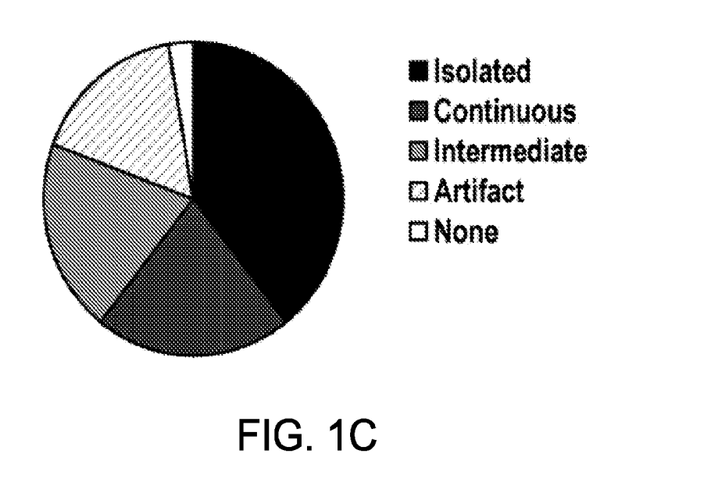

Time-compressed bipolar EEG recordings were visually examined for changes associated with ECoG-identified spreading depolarizations. It was found that nearly all ECoG-identified events had clear manifestations as depressions in EEG amplitudes. For each depolarization, depressions were categorized as one of three types: isolated, continuous, or intermediate (FIG. 1, Table 2). In very specific embodiments, features indicating spreading depolarization comprise isolated depressions. Isolated depressions were observed in 179 of 455 cases (39%), and were characterized as being unique to individual spreading depolarizations, with a slow onset of depressed EEG amplitude followed by a slow recovery to baseline or partial recovery to a new baseline (e.g. FIG. 1, FIG. 2B and FIG. 4). For these events, a maximal depression to 57% (median; IQR 44-67) of baseline amplitude developed over 11.1 min (median; IQR 8.0-15.5) and the total time envelope of depression was 21 min (median, IQR 16-33).

In 9 instances (e.g. FIG. 1), the EEG amplitude depression induced by an initial depolarization was sustained by subsequent depolarizations that occurred prior to amplitude recovery. Thus, these subsequent depolarizations (e.g. FIG. 1), occurring with short inter-event intervals (median 34 min; IQR 30-40), were categorized as having continuous-type depression periods. In other specific embodiments, features indicating spreading depolarization comprise continuous depression reflecting two or more sequential depressions, in some instances overlapping so that amplitude is not recovered in between depressions. For 8 of 9 continuous depression periods in which amplitude recovery was recorded, the total number of depolarizations ranged from 2 to 11, and total depression durations ranged from 55 min to over 6 h.

This pattern of continuous, prolonged EEG depression during repetitive spreading depolarizations was also evidenced in 3 patients (nos. 8,11,15) from the onset of EEG

TABLE 2

Summary of EEG manifestions of spreading depolarizations

| Patient No. | ECoG Strip Location | EEG Channels with Depressions | ˆSpread in EEG (No.) | ECoG *No. Spread. Depolar. | EEG Isolated | Cont. | Intermed. | Artif. | No Change |
|---|---|---|---|---|---|---|---|---|---|
| 2 | R FP | — | — | 1 | — | — | — | — | 1 |
| 4 | R T | — | — | 3 | — | — | — | — | 3 |
| 5 | R FP | Fp2-F8 | No | 1 | 1 | — | — | — | — |
| 6 | R Sup P | Fp2-F4, F4-C4, C4-P4, P4-O2, T8-P8, P8-O2 | Yes (15) | 36 | 27 | — | 1 | 8 | — |
| 8 | L P | F3-C3, C3-P3, P3-O1, F7-T7, T7-P7 | Yes (6) | 24 | 10 | 14 | — | — | — |
| 9 | R FP | Fp2-F4, F4-C4 | No | 83 | 19 | 14 | 45 | 3 | 2 |
| 11 | R FB | Fp2-F4 | No | 16 | 5 | 11 | — | — | — |
| 12 | L F | Fp1-F3 | No | 1 | 1 | — | — | — | — |
| 15 | R F | Fp2-F4, F4-C4 | No | 45 | 3 | 42 | — | — | — |
| 16 | L FP | Fp1-F3, F3-C3, C3-P3, P3-O1 | Yes (7) | 125 | 45 | 5 | 24 | 49 | 2 |
| 17 | R FP | Fp2-F4, F4-C4, C4-P4, P4-O2, Fp2-F8, F8-T8, T8-P8 | Yes (28) | 115 | 66 | 11 | 21 | 16 | 1 |
| 18 | L O | T7-P7, P7-O1 | Yes (2) | 5 | 2 | — | — | — | 3 |

Figure 2A:
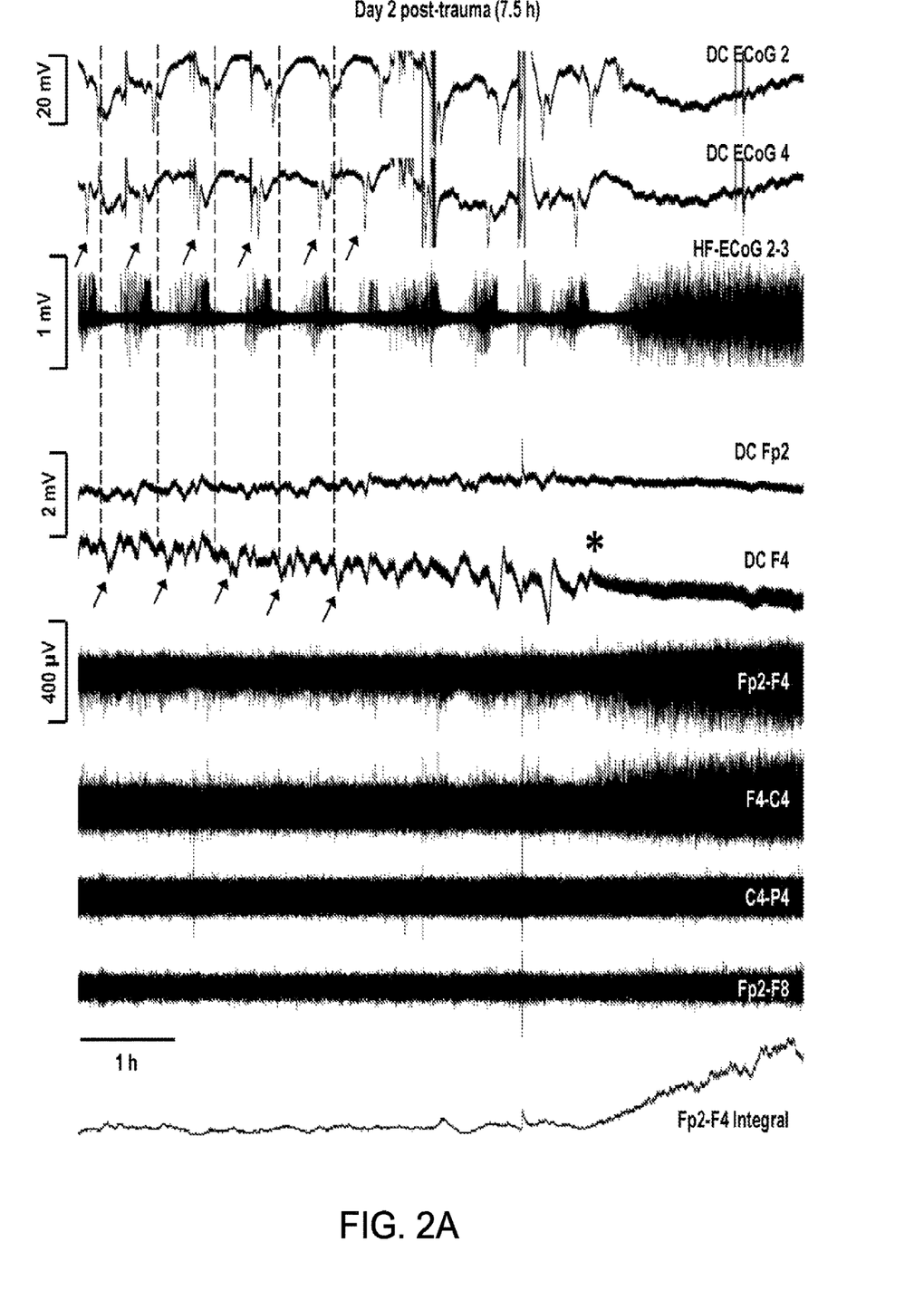

EcoG strips were located in frontal (F), temporal (T), occipital (O), frontobasal (FB), frontoparietal (FP), or superior parietal (Sup P) locations of left (L) or right (R) hemisphere. ˆIndicates whether depression of EEG activity was observed as spreading depolarizations; the number is given in parentheses. *Number of ECoG-identified spreading depolarizations during period of simultaneous EEG/ECoG monitoring. For each patient, the number of depolarizations with each type of EEG manifestation is given. Isolated types induced EEG depression and were scored for depression depth and duration; continuous types exhibited sustained depression from a prior depolarization; intermediate types were associated with only partial recover from prior depolarizations and no clear further depression of amplitudes; recordings were sometimes contaminated with artifact, precluding assessment for some depolarizations; no EEG changes were observed.

recordings. In these cases, depolarizations were ongoing at the start of EEG recordings and therefore the onset of EEG depression with the first depolarization was not witnessed. However, in each case, the EEG amplitude recovered when repetitive depolarizations stopped. An example is shown in FIG. 2A. In total, 97 of 455 ECoG-identified depolarizations (21%) were associated with continuous EEG depressions sustained by multiple depolarizations. Intervals between depolarizations with continuous-type EEG depressions (median 33 min; IQR 27-38) were significantly shorter than intervals preceding depolarizations with isolated-type EEG depressions (median 64 min; IQR 43-133; p<0.001, M-W).

Of the remaining depolarizations, for 76 events there was substantial artifact in the EEG signal, and therefore the power integral, that precluded observation and/or scoring of the event. In a further 12 cases, no EEG depressions were observed to be induced by the depolarizations or to be continuing from previous ones.

Figure 3A:
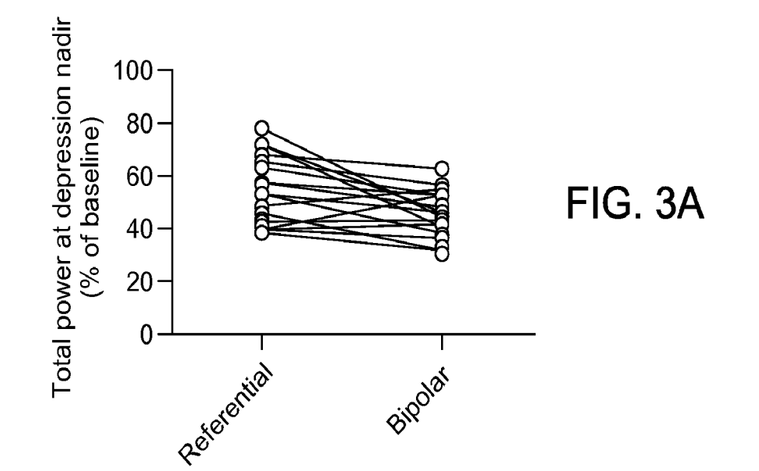

To determine whether depressions of EEG amplitude might be better identified in monopolar recordings, depression magnitudes were compared between bipolar and monopolar (referential) channel derivations in the 7 patients with at least 3 isolated-type depolarizations. Amplitudes were significantly more depressed in bipolar recordings, reaching 47% of baseline values, compared to monopolar recordings with depression to only 55% of baseline (p<0.01, paired t-test, n=3 per patient; FIG. 3A). In very specific embodiments, channels comprise bipolar channels.

Figure 2B:
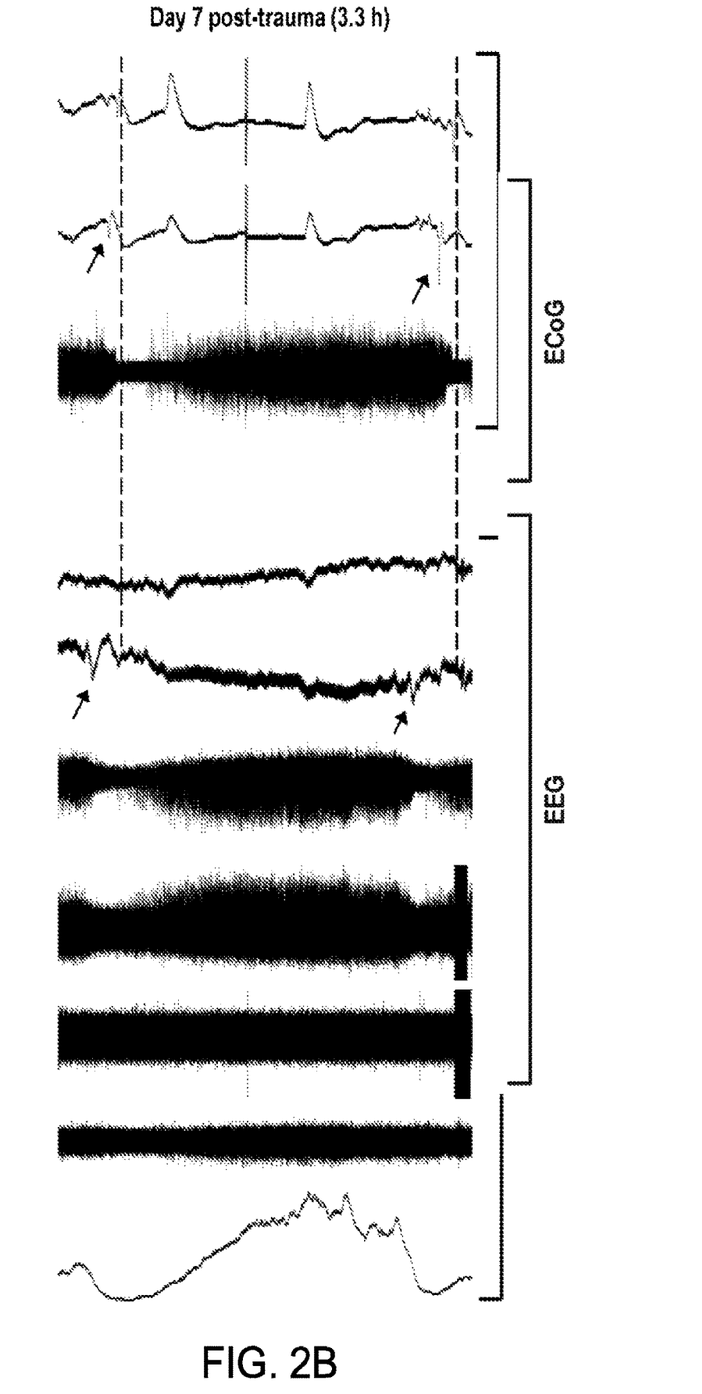
Figure 5B:
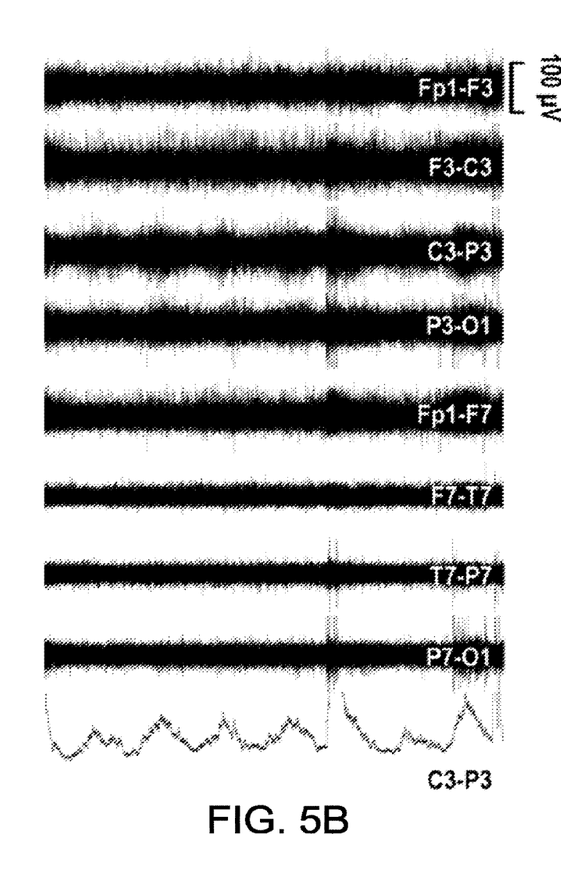

Table 3 summarizes the EEG abnormalities noted in clinical reports, including epileptiform discharges and seizures.

lower amplitude signals of other ipsilateral (e.g. Fp1-F3, P7-O1) and all contralateral channels. Thus, spreading depolarizations were manifested as EEG depressions in these channels by suppressing a high-amplitude baseline such that, during maximal depression, amplitudes were similar across all channels. Accordingly, the degree of amplitude depression positively correlates with the baseline EEG amplitude prior to depression, which was observed for 3 of 5 patients with >10 isolated-type depressions (R2 range 0.46-0.67, p's<0.001). Similar examples of this phenomenon for isolated-type depressions are shown in FIGS. 2B and 5B.

Other embodiments are directed to methods of treating a brain injury patient by reducing extent of injury secondary to a primary lesion. The method comprises: (a) initiating a continuous scalp EEG recording of the patient; (b) identifying at least one EEG channel exhibiting high-amplitude delta activity and recording a baseline EEG pattern at the at least one channel; wherein the recordings are translated to a compressed time scale; (c) monitoring the continuous scalp EEG recording at the least one channel for presence of a feature indicative of a spreading depolarization, wherein the feature comprises at least one of (i) a depression in the high-amplitude delta activity in the EEG recording relative to the baseline recording pattern, and (ii) a shift in direct-current potential in the EEG recording relative to the baseline recording pattern; and (d) initiating therapy effective to inhibit spreading depolarization upon detection of a spreading depolarization, thereby reducing extent of injury secondary to the primary lesion.

TABLE 3

Clinical assessment of EEG abnormalities

| No. | Gen. Slowing | Focal Slowing | Epileptiform Discharges | EEG Seizures | ECoG Seizures (No., Duration) | Breach | Other |
|---|---|---|---|---|---|---|---|
| 1 | Sev, Mod-sev | L FT CPDA | L TP | — | | Y | SIRPIDs |
| 2 | Sev, Mod | R hem CPDA | R FC | — | | Y | |
| 3 | Sev | Bilat F delta | — | — | | Y | |
| 4 | Sev | R FCT C/IPDA | Freq R FCP | 25 R FC | | Y | |
| 5 | Sev, Mod | R hem CPDA | — | — | | Y | BS |
| 6 | Mod-sev, Mod | R FCT CPDA | R FC | — | | Y | |
| 7 | Sev, Mod, Mild | R hem CPDA | — | — | | Y | |
| 8 | Sev, Mod-sev | L FT CPDA | Rare L C | — | | Y | |
| 9 | Sev, Mod-sev | PDA, R > L | Freq R FC, R CP, L FC | — | | Y | SIRPIDs |
| 10 | Sev, Mod, Mild | R FCT CPDA | Rare R CP | — | | Y | |
| 11 | Sev, Mod | R FCT C/IPDA | Freq R FC | Freq R F | 105, 221 min | Y | |
| 12 | Sev, Mod-sev | L hem CPDA | Rare L FC, CP | — | | Y | |
| 13 | Mild-mod | L hem CPDA | Rare L C | Freq L F | 161, 317 min | Y | PLEDs |
| 14 | Sev, Mild | Bilat F IPDA | — | — | | Y | |
| 15 | Sev | R FCT CPDA | — | — | | Y | |
| 16 | Sev | L FCP CPDA | Rare L CP | — | 26, 103 min | Y | |
| 17 | Sev | R hem CPDA | R F, R P | — | | Y | PLEDs |
| 18 | Mod | L hem IPDA | Intermit L CP | — | | Y | SIRPIDs |

EEG abnormalities described in clinical reports of epileptologists. When given, locations were abbreviated as R = right, L = left, F = frontal, C = central, P = parietal, T = temporal, Bilat = bilateral, hem = hemispheric. Generalized slowing is described as severe, moderate, or mild. Focal slowing is described as continuous and/or intermittent polymorphic delta activity (C/IPDA). Epileptiform discharges are described as frequent, intermittent, or rare. All EEG seizures were non-convulsive, and all patients had breach rhythm. Other abnormalities described in reports are SIRPIDs = Stimulus-induced rhythmic periodic, or ictal discharges. BS = burst suppression, and PLEDs = periodic lateralized epileptiform discharges.

All patients exhibited focal slowing consisting of high-amplitude polymorphic delta activity. Depolarization-induced amplitude depressions of all 3 types were caused primarily by suppression of this high-amplitude delta activity, rather than by suppression of a normal-amplitude baseline activity. In FIG. 1, for instance, polymorphic delta activity elevates baseline amplitudes in several channels of the injured hemisphere (e.g. C3-P3, T7-P7), in contrast to A suitable therapy may be selected by the clinician based on the nature and cause of the primary brain lesion or insult to the patient's brain. Causes of lesions known to be frequently accompanied by spreading depolarizations include ischemic brain injury, hemorrhagic brain injury, or traumatic brain injury. Further, a suitable therapy may be directed or supplemented by direct treatment of the brain to inhibit spreading depolarizations. Generally, spreading depolarizations are known to decrease brain concentrations of inhibitory neurotransmitters such as gamma-amino butyric acid and serotonin. This makes the brain more vulnerable to seizure activity and other conditions associated with CNS excitability. Non-limiting examples of neuroprotective therapies which may reduce spreading depolarizations include administering one or more of an N-methyl-D-aspartate receptor antagonist, magnesium, a voltage-sensitive calcium channel antagonist, an inhibitory neurotransmitter receptor agonist or re-uptake inhibitor, an antioxidant, a free radical scavenger, caffeine with or without ethanol, estrogen, progesterone, ginssenoside, selegiline and nicotine; and/or instigating hypothermia. Administration of agents effective to increase concentration of inhibitory neurotransmitters, including serotonin and gamma-amino butyric acid, may be particularly effective in protecting the brain against secondary injury due to spreading depolarizations.

Once a therapy is initiated, efficacy may be monitored and therapy may be adjusted in accordance with the observed effect on spreading depolarizations. In some embodiments, monitoring therapy comprises recording a continuous scalp EEG of the patient subsequent to the step of initiating therapy and adjusting the therapy according to whether absence, detection with decrease in frequency and/or duration of spreading depolarization, detection without a decrease in frequency and/or duration of spreading depolarization, or detection with an increase in one or both of frequency and duration the spreading depolarization. The observed effects may result from treating the primary brain injury or from treating the brain or CNS to recover from a spreading depolarization. In either case a secondary injury may be ameliorated or substantially avoided.

FIG. 2A further illustrates a case in which all ipsilateral channels have similar amplitude due to suppression of high-amplitude delta in Fp2-F4 and F4-C4 during a series of repetitive spreading depolarizations. When depolarizations cease, high-amplitude delta activity emerges, revealing the former state as 'depressed'. Polymorphic delta was restricted to 1-2 channels in some patients, but was widespread through most of the injured hemisphere in others. EEG amplitude depressions were rarely observed in channels without high-amplitude delta activity, although high-amplitude delta was sometimes present in channels beyond those exhibiting depressions.

Figure 3B:
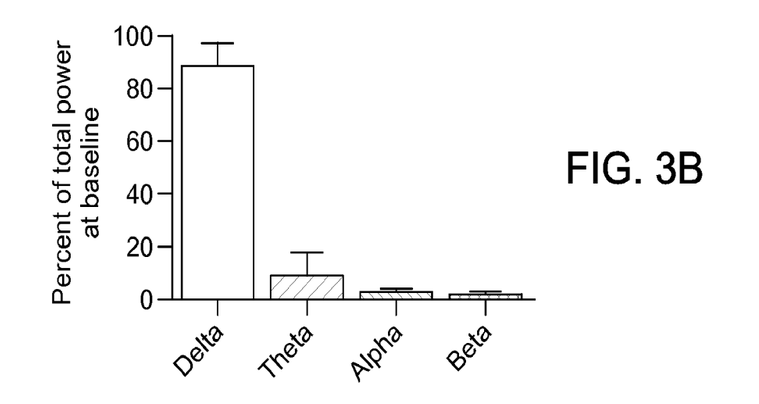
Figure 3C:
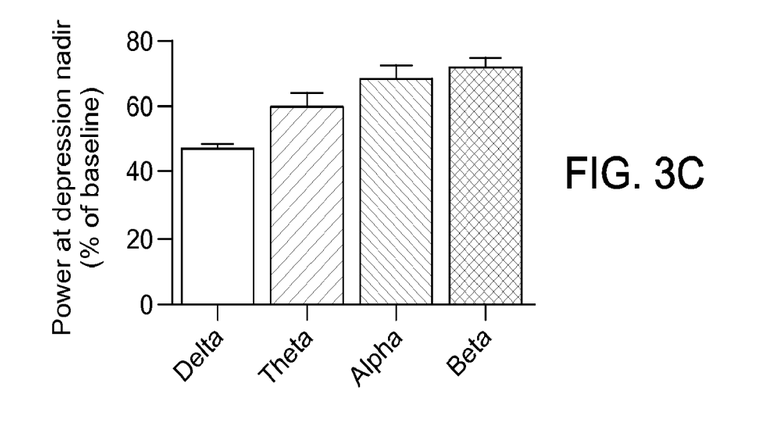

The role of delta activity in observing spreading depolarizations in the EEG was confirmed in quantitative analysis. Baseline EEG activity prior to isolated-type depressions was dominated by delta (0.5-4.0 Hz), which accounted for 89% of total power (FIG. 3B). Thus, suppression of delta activity accounts for nearly all of the absolute magnitude of amplitude depression induced in the EEG by spreading depolarizations. Furthermore, the relative suppression of delta activity was also greater than for higher frequency bands: delta was depressed to a mean 47% of baseline power, while higher bands had progressively less depression (FIG. 3C).

In 3 of the 10 patients for whom EEG amplitude depressions were observed, changes were restricted to a single bipolar EEG channel (nos. 5,11,12). In the other 7 patients, spreading depolarizations induced EEG depressions in 2 to 6 channels, in some cases spanning broad expanses of the ipsilateral hemisphere (Table 2). In 5 of these 7 patients, 62 of 179 isolated-type events (35%) showed a clear spread of the amplitude depression with a distinct time delay between depression onset in different channels. Examples from two patients are shown in FIG. 4 (see also FIG. 1). For each depolarization, time intervals between nadirs of the amplitude depressions of the 2 channels with the clearest signals, and not sharing a common electrode, were measured. These intervals were 17 min (median; IQR 11-34) and did not significantly differ by the distance separating the electrode pairs. In three patients (nos. 6, 16, 17), spreading depolarizations induced spreading EEG depressions in the most anterior and posterior channels (e.g. Fp2-F4 and P4-O2), indicating widespread propagation throughout the ipsilateral cerebral cortex.

Shifts of the extracellular direct-current (DC) potential are a signature of spreading depolarization, reflecting the mirror image of sustained intracellular depolarization. In 4 patients with both spreading depolarizations and DC-coupled EEG recordings, monopolar channels were examined for the presence of DC shifts accompanying depressions of the conventional frequency band (0.5-50 Hz). In the majority of cases, DC shifts could not be identified. However, clear instances were found in 3 of 4 patients (nos. 15,17,18) with peak-to-peak amplitudes of 708 V (mean; SD 242, n=37), 333 V (mean; SD 60, n=6), and 432 V (n=2), respectively. In patient no. 15, DC shifts were observed during a cluster of 42 repetitive spreading depolarizations that spanned a total of 26 hours. During this time, high-frequency EEG activity was continuously depressed and the DC shifts appeared as a highly unstable, continuously fluctuating baseline potential (FIG. 2A). The DC shifts propagated between electrodes Fp2 and F4 with a delay of 9.3 min (mean, SD 2.3, n=25). The cessation of depolarizations was then signaled by a marked EEG state change: the DC potential became steady and the amplitude of 0.5-50 Hz activity recovered from the depressed state. A similar fluctuating DC potential was observed in patient no. 17 during a cluster of 11 depolarizations spanning 7 h of continuous depression, though the DC shifts corresponding to individual depolarizations could not be deciphered.

The EEG signatures of spreading depolarizations were clear enough that the occurrence of repetitive events could be identified without simultaneous ECoG recordings. In three patients, ECoG was interrupted for several hours while EEG recordings continued. FIG. 5 shows examples from two patients in which cyclic depressions of the EEG amplitude and integrals clearly identify ongoing depolarization activity.

Three patients had recurrent seizures in ECoG recordings (Table 3). For 2 patients (nos. 11,16), seizures occurred at a single electrode and consisted of 1-3 Hz discharges with evolving amplitude and frequency. Individual seizures were 1-12 min in duration and recurred at intervals of 3 to 30 min. Cumulative seizure durations were 221 min (105 episodes) and 103 min (26 episodes) for patients 11 and 16, respectively. Corresponding EEG seizures were identified in patient 11 but not 16. In the third patient (no. 13), seizures were more widespread, involving 3-6 ECoG electrodes, and occurred separately at two foci at different ends of the electrode strip positioned in the lateral frontal lobe from inferior to superior. Accordingly, these seizures were observed separately at inferior (F7, T7) and superior (F3, C3, P3) EEG electrodes as partial non-convulsive status epilepticus. From a background of pseudoperiodic 1-Hz discharges with steady amplitude, seizures emerged in ECoG with evolving amplitude, frequency and complexity every 10-15 min, lasting 1-3 min. In total, 161 seizures occurred for a cumulative duration of 317 min.

The features observable from a scalp EEG may be characterized by severity with respect to the potential to cause secondary injury. Therefore, continuous scalp EEG recording affords a convenient, relatively low-cost and non-invasive method for triaging brain-injured patients. This may be particularly useful in mass disasters or in military contexts. One embodiment of a method for triage of brain injury patients comprises generating a continuous scalp EEG recording of the patients, identifying patients exhibiting high-amplitude delta activity in at least one EEG channel of the recording, monitoring the EEG recording of the identified patients in the at least one channel across a time frame for the presence of at least one feature indicative of a spreading depolarization; and assigning a greater degree of urgency to a patient based on detection of an SD. Features include an isolated depression in the high-amplitude delta activity, and/or a shift in direct-current potential across a time frame. Degree of urgency may also be assigned on one or more characteristics of the features observed. For example, frequency of a feature or total duration of a feature across a time frame are factors which predict outcome. Patients with a greater frequency or more total duration of a feature are assigned a greater urgency than patients with a lower frequency or lesser total duration, the terms "more and lesser" being ascertained relative to the patient group being triaged. In some embodiments, patients exhibiting a feature at more than one channel with a time delay are assigned higher urgency than patients exhibiting a feature at one channel, and patients exhibiting a continuous feature are assigned higher urgency than patients exhibiting an isolated feature.

Where elements are presented as lists, it is to be understood that each subgroup of the elements is also disclosed, and any element(s) can be removed from the group. The invention provides all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, any particular embodiment, aspect, element, feature, etc., of the present invention may be explicitly excluded from any one or more of the claims.

The invention claimed is:

1. A non-invasive method of detecting a spreading depolarization secondary to a brain injury in a patient and reducing extent of a secondary brain injury, the method comprising:
    (a) recording a baseline scalp electroencephalogram (EEG) pattern at a compressed time scale of 40-90 mm/hr of an injured brain hemisphere of the patient in at least one bipolar channel;
    (b) recording a continuous scalp EEG pattern in the patient at the compressed time scale of 40-90 mm/hr across a time frame in the at least one bipolar channel to record a baseline; and
    (c) detecting a spreading depolarization during the time frame by observing a depression in delta activity across a depression period from the baseline in the recorded continuous scalp EEG pattern relative to the recorded baseline scalp EEG pattern recording in the at least one bipolar channel, and
    (d) initiating neuroprotective therapy effective to reduce frequency and duration of spreading depolarization when spreading depolarization is detected in (c).

2. The non-invasive method according to claim 1, wherein the depression period is defined from onset of a depression until recovery to a steady-state amplitude.

3. The non-invasive method according to claim 1, further comprising verifying the spreading by observing in two or more channels with a time delay between onset.

4. The non-invasive method according to claim 3, wherein all channels are intra-hemispheric.

5. The non-invasive method according to claim 2, wherein an observed depression comprises an isolated depression across the depression period.

6. The non-invasive method according to claim 1, wherein an observed depression comprises continuous depression across the depression period.

7. The non-invasive method according to claim 1, wherein at least eight EEG electrodes are located across the injured brain hemisphere.

8. The non-invasive method according to claim 1, wherein the steps of recording are effectuated with DC-coupled EEG amplifiers.

9. The non-invasive method according to claim 1, wherein the depression comprises a spreading shift in direct-current potential occur in a 0.0 to 0.05 Hertz frequency band.

10. The method of claim 9, wherein the spreading shift in direct-current potential comprises an isolated shift or a continuous shift.

11. The method of claim 9, wherein the spreading shift in direct-current potential is observed in a single EEG channel.

12. The method of claim 9, wherein the spreading shift in direct-current potential occurs in two or more EEG channels with a time delay between onset.

13. The method of claim 1, wherein the continuous scalp EEG pattern is a measurement of direct current potential.

14. The method of claim 1, wherein the depression in delta activity is of up to 47% from the baseline.

* * * * *